(12) United States Patent
Arai

(10) Patent No.: US 11,517,280 B2
(45) Date of Patent: *Dec. 6, 2022

(54) IMAGE PROCESSING APPARATUS, METHOD, AND PROGRAM

(71) Applicant: FUJIFILM Corporation, Tokyo (JP)

(72) Inventor: Takahisa Arai, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 119 days.

This patent is subject to a terminal disclaimer.

(21) Appl. No.: 16/925,776

(22) Filed: Jul. 10, 2020

(65) Prior Publication Data

US 2021/0030384 A1 Feb. 4, 2021

(30) Foreign Application Priority Data

Jul. 29, 2019 (JP) .............................. JP2019-138865

(51) Int. Cl.
A61B 6/00 (2006.01)
A61B 6/04 (2006.01)
(Continued)

(52) U.S. Cl.
CPC .............. A61B 6/502 (2013.01); A61B 6/025 (2013.01); A61B 6/463 (2013.01); A61B 6/5217 (2013.01);
(Continued)

(58) Field of Classification Search
CPC ....... A61B 6/025; A61B 6/469; A61B 6/5223; A61B 6/486; A61B 6/463; A61B 6/08;
(Continued)

(56) References Cited

U.S. PATENT DOCUMENTS 6,611,575 B1 * 8/2003 Alyassin .............. G01N 23/044
378/197
8,983,156 B2  3/2015 Periaswamy et al.
(Continued)

FOREIGN PATENT DOCUMENTS

JP    H07-194598 A    8/1995
JP    2006-130223 A   5/2006
(Continued)

OTHER PUBLICATIONS

The extended European search report issued by the European Patent Office dated Feb. 8, 2021, which corresponds to European Patent Application No. 20196187.7-1126 and is related to U.S. Appl. No. 16/925,776.
(Continued)

*Primary Examiner* — Irakli Kiknadze
(74) *Attorney, Agent, or Firm* — Studebaker & Brackett PC

(57) ABSTRACT

A reconstruction unit generates a plurality of tomographic images representing a plurality of tomographic planes of a subject by reconstructing a plurality of projection images acquired by performing tomosynthesis imaging. A synthesis unit synthesizes the plurality of tomographic images to generate a composite two-dimensional image. A display control unit displays the composite two-dimensional image on a display, and in a case where one tissue of a first tissue and a second tissue that are present in the subject in association with each other is selected in the displayed composite two-dimensional image, emphasizes and displays the selected one tissue and the other tissue associated with the selected one tissue.

7 Claims, 8 Drawing Sheets

(51) Int. Cl.
  *A61B 6/02* (2006.01)
  *G06T 7/00* (2017.01)
  *G06T 11/00* (2006.01)

(52) U.S. Cl.
  CPC .......... *A61B 6/5223* (2013.01); *G06T 7/0012* (2013.01); *G06T 11/003* (2013.01); *G06T 2207/10072* (2013.01); *G06T 2207/30068* (2013.01)

(58) Field of Classification Search
  CPC ......... A61B 6/466; A61B 6/032; A61B 6/545; A61B 8/5223; A61B 6/502; A61B 8/0825; A61B 6/5217; A61B 5/4312; A61B 6/4035; A61B 6/4085; A61B 6/4241; A61B 6/4291; A61B 6/482; A61B 6/484; A61B 6/5235; A61B 6/4452; A61B 6/54; A61B 6/467; A61B 6/0414; A61B 6/4476; A61B 6/0487; G06T 7/11; G06T 11/008; G06T 7/0012; G06T 7/174; G06T 11/001; G06T 7/48; G06T 11/005; G06T 2207/10081; G06T 2207/20212; G06T 11/003; G06T 5/50; G06T 2211/436; G06T 2207/10072; G06T 2207/20221; G06T 2207/10112; G06T 2207/30068; G06T 2207/30096; G06T 11/006; G06T 7/0016; G06T 2210/41; G06T 7/0014; G06T 2207/10116; G16H 50/30; H04N 1/6027; H04N 1/465; G06V 10/56; G06V 10/54; G06V 10/462; G01N 23/087; G01N 23/20091
  USPC .................................................. 378/4, 20, 62
  See application file for complete search history.

(56) References Cited

U.S. PATENT DOCUMENTS

| | | | |
|---|---|---|---|
| 9,792,703 | B2 | 10/2017 | Costa et al. |
| 2008/0019581 | A1 | 1/2008 | Gkanatsios et al. |
| 2009/0123052 | A1 | 5/2009 | Ruth et al. |
| 2009/0141955 | A1 | 6/2009 | Morita |
| 2011/0109650 | A1 | 5/2011 | Kreeger et al. |
| 2012/0069951 | A1 | 3/2012 | Toba |
| 2014/0015856 | A1 | 1/2014 | Xiao et al. |
| 2014/0093029 | A1 | 4/2014 | Masumoto et al. |
| 2014/0226783 | A1* | 8/2014 | Ning .................... G01N 23/087 378/19 |
| 2014/0327702 | A1 | 11/2014 | Kreeger et al. |
| 2015/0356732 | A1 | 12/2015 | Fukuda |
| 2015/0379374 | A1 | 12/2015 | Fukuda |
| 2016/0051215 | A1 | 2/2016 | Chen et al. |
| 2018/0055459 | A1 | 3/2018 | Fukuda |
| 2018/0109698 | A1* | 4/2018 | Ramsay ................. G16H 50/30 |
| 2018/0174341 | A1 | 6/2018 | Palma et al. |
| 2019/0059838 | A1 | 2/2019 | Shimada |
| 2019/0162679 | A1* | 5/2019 | Yamakawa .......... G01V 5/0016 |
| 2020/0372693 | A1* | 11/2020 | Kobayashi ............ A61B 6/025 |
| 2021/0082095 | A1* | 3/2021 | Fukuda .................. A61B 6/463 |

FOREIGN PATENT DOCUMENTS

| | | |
|---|---|---|
| JP | 2008-068032 A | 3/2008 |
| JP | 2009-136376 A | 6/2009 |
| JP | 2012-061196 A | 3/2012 |
| JP | 2014-014679 A | 1/2014 |
| JP | 2014-068752 A | 4/2014 |
| JP | 2014-128716 A | 7/2014 |
| JP | 2014-183876 A | 10/2014 |
| JP | 2014-188250 A | 10/2014 |
| JP | 2016-510669 A | 4/2016 |
| JP | 2018-029746 A | 3/2018 |
| JP | 2019-037576 A | 3/2019 |

OTHER PUBLICATIONS

An Office Action mailed by the United States Patent and Trademark Office dated Mar. 4, 2022, which corresponds to U.S. Appl. No. 17/002,716 and is related to U.S. Appl. No. 16/925,776.

An Office Action mailed by the Japanese Patent Office dated Jun. 7, 2022, which corresponds to Japanese Application No. 2019-168506 with English translation.

An Office Action mailed by the United States Patent and Trademark Office dated Jun. 30, 2022, issued in U.S. Appl. No. 16/925,776, which is related to U.S. Appl. No. 16/925,776.

An Office Action; "Notice of Reasons for Refusal," mailed by the Japanese Patent Office dated Jun. 21, 2022, which corresponds to Japanese Patent Application No. 2019-138865 and is related to U.S. Appl. No. 16/925,776; with English language translation.

An Office Action mailed by the Japanese Patent Office dated Oct. 4, 2022, which corresponds to Japanese Application No. 2019-168506 with English translation.

Advisary Action mailed by the United States Patent and Trademark Office dated Oct. 17, 2022, issued in U.S. Appl. No. 16/925,776, which is related to U.S. Appl. No. 16/925,776.

An Office Action mailed by the Japanese Patent Office dated Oct. 18, 2022, which corresponds to Japanese Application No. 2019-138865 with English translation.

* cited by examiner

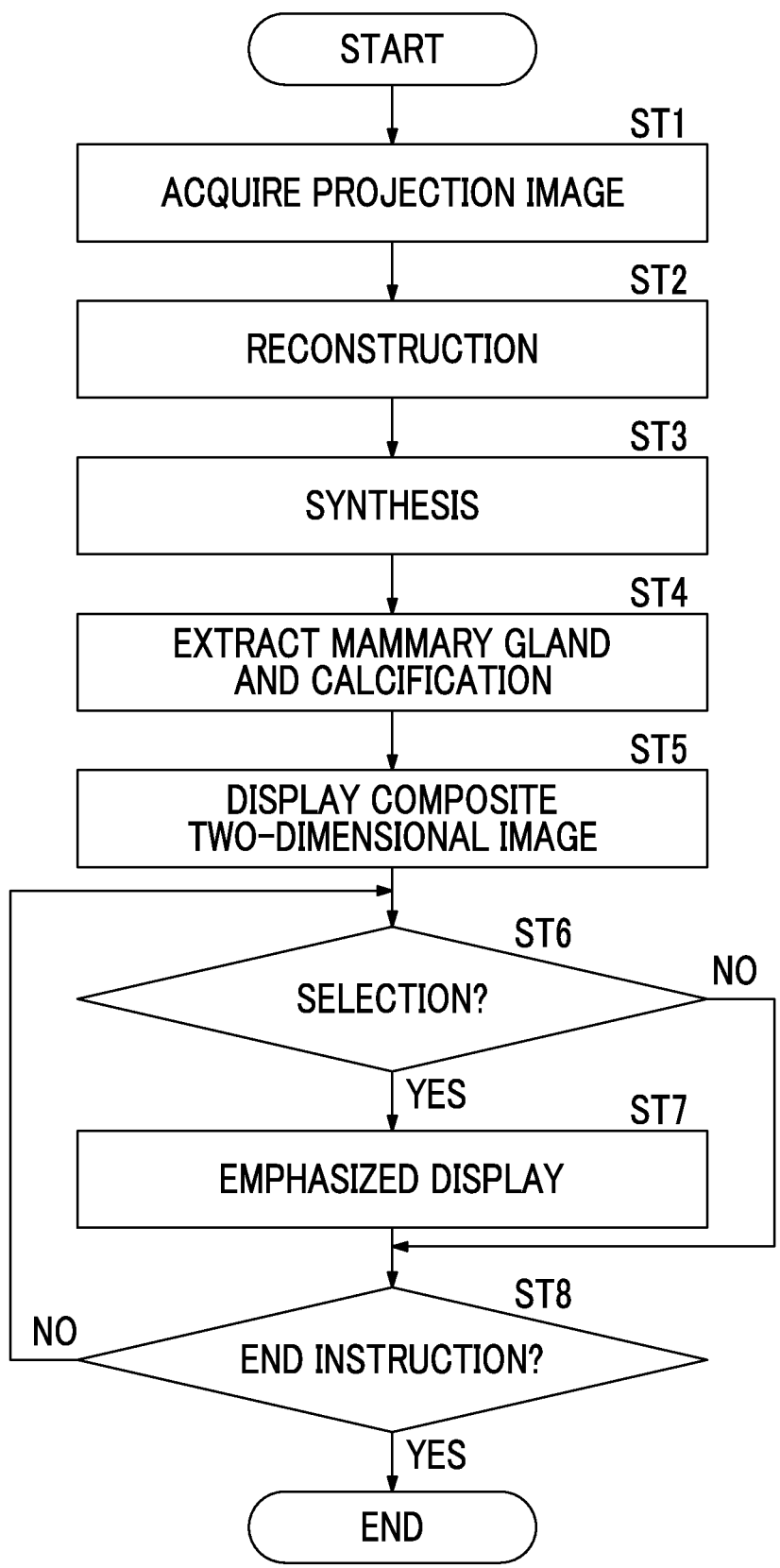

IMAGE PROCESSING APPARATUS, METHOD, AND PROGRAM

CROSS REFERENCE TO RELATED APPLICATIONS

The present application claims priority under 35 U.S.C. § 119 to Japanese Patent Application No. 2019-138865 filed on Jul. 29, 2019. The above application is hereby expressly incorporated by reference, in its entirety, into the present application.

BACKGROUND

Technical Field

The present disclosure relates to an image processing apparatus, a method, and a program.

Related Art

In recent years, in order to promote early detection of breast cancer, image diagnosis using a radiation image capturing apparatus (called mammography) for imaging a breast has attracted attention. Further, tomosynthesis imaging has been proposed in which in the mammography, imaging is performed by moving a radiation source to irradiate a breast with radiation at a plurality of radiation source positions and a plurality of projection images acquired by the imaging are added up to generate a tomographic image in which a desired tomographic plane is emphasized. In the tomosynthesis imaging, a plurality of projection images are acquired by imaging the breast at a plurality of radiation source positions by moving the radiation source in parallel to a radiation detector or moving the radiation source so as to draw a circular or elliptical arc according to the characteristics of the imaging apparatus and required tomographic images, and the projection images are reconstructed using, for example, a back projection method, such as a simple back projection method or a filtered back projection method, to generate a tomographic image.

By generating such a tomographic image on a plurality of tomographic planes of the breast, it is possible to separate structures overlapping each other in a depth direction in which the tomographic planes are aligned, in the breast. For this reason, it is possible to find the lesion difficult to be detected in a two-dimensional image acquired by simple imaging in the related art (hereinafter, referred to as a simple two-dimensional image).

A technique has been known in which a pseudo two-dimensional image (hereinafter, referred to as a composite two-dimensional image) corresponding to the simple two-dimensional image is generated by adding a plurality of the tomographic images that are acquired by tomosynthesis imaging and have different distances (a position in a height direction) toward the radiation source side from the detection surface of the radiation detector (JP2014-128716A).

However, since the composite two-dimensional image is generated by adding the tomographic images, the lesion such as calcification and the mammary gland overlap, and the three-dimensional positional information of the lesion and the mammary gland is lost. Therefore, a technique has been proposed in which calcification and the mammary gland are extracted from the tomographic image, and the mammary gland is distinguished and displayed based on the calcification in the composite two-dimensional image (see JP2019-037576A). According to the technique disclosed in JP2019-037576A, calcification and the mammary gland can be easily distinguished.

In the image diagnosis of the breast, in a case where calcifications sporadically occur in the breast, the calcifications are often relatively benign. On the other hand, in a case where calcifications are distributed along the mammary gland, the calcification is associated with the mammary gland, and thus is often malignant. Although the technique disclosed in JP2019-037576A can easily distinguish calcification and mammary gland in the composite two-dimensional image, the relevance of the mammary gland and calcification cannot be easily recognized. Therefore, in the image diagnosis of the breast, it is conceivable to display the tomographic images one by one and perform image reading while marking the calcification and the mammary gland. However, such a method of image reading has a great burden on a doctor who performs image reading.

SUMMARY OF THE INVENTION

The present disclosure has been made in view of the above circumstances, and an object of the present disclosure is to recognize relevance of tissues, such as a mammary gland and calcification, included in a subject in a composite two-dimensional image acquired by tomosynthesis imaging.

An image processing apparatus according to the present disclosure comprises a reconstruction unit that generates a plurality of tomographic images representing a plurality of tomographic planes of a subject by reconstructing a plurality of projection images corresponding to a plurality of radiation source positions which are generated by causing an imaging apparatus to perform tomosynthesis imaging in which a radiation source is moved relative to a detection unit to irradiate the subject with radiation at the plurality of radiation source positions according to movement of the radiation source, a synthesis unit that synthesizes the plurality of tomographic images to generate a composite two-dimensional image, and a display control unit that displays the composite two-dimensional image on a display unit, and in a case where one tissue of a first tissue and a second tissue that are present in the subject in association with each other is selected in the displayed composite two-dimensional image, emphasizes the selected one tissue and the other tissue associated with the selected one tissue.

In the image processing apparatus according to the present disclosure, the synthesis unit may generate the composite two-dimensional image by weighted-adding pixel values of pixels corresponding to the plurality of tomographic images.

The image processing apparatus according to the present disclosure may further comprise an extraction unit that extracts the first tissue and the second tissue from the plurality of tomographic images.

In the image processing apparatus according to the present disclosure, the extraction unit may extract the first tissue and the second tissue based on an instruction by an operator with respect to the plurality of tomographic images displayed on the display unit.

In the image processing apparatus according to the present disclosure, the subject may be a breast, the first tissue may be a mammary gland, and the second tissue may be calcification.

An image processing method according to the present disclosure comprises generating a plurality of tomographic images representing a plurality of tomographic planes of a subject by reconstructing a plurality of projection images corresponding to a plurality of radiation source positions which are generated by causing an imaging apparatus to perform tomosynthesis imaging in which a radiation source is moved relative to a detection unit to irradiate the subject with radiation at the plurality of radiation source positions according to movement of the radiation source, synthesizing the plurality of tomographic images to generate a composite two-dimensional image, and displaying the composite two-dimensional image on a display unit, and in a case where one tissue of a first tissue and a second tissue that are present in the subject in association with each other is selected in the displayed composite two-dimensional image, emphasizing and displaying the selected one tissue and the other tissue associated with the selected one tissue.

The image processing method according to the present disclosure may be provided as a program causing a computer to execute.

Another image processing apparatus according to the present disclosure comprises a memory that stores a command to be executed by a computer, and a processor configured to execute the stored commands, in which the processor executes generating a plurality of tomographic images representing a plurality of tomographic planes of a subject by reconstructing a plurality of projection images corresponding to a plurality of radiation source positions which are generated by causing an imaging apparatus to perform tomosynthesis imaging in which a radiation source is moved relative to a detection unit to irradiate the subject with radiation at the plurality of radiation source positions according to movement of the radiation source, synthesizing the plurality of tomographic images to generate a composite two-dimensional image, and displaying the composite two-dimensional image on a display unit, and in a case where one tissue of a first tissue and a second tissue that are present in the subject in association with each other is selected in the displayed composite two-dimensional image, emphasizing and displaying the selected one tissue and the other tissue associated with the selected one tissue.

According to the present disclosure, it is easy to recognize the relevance of a first tissue and a second tissue included in the subject.

BRIEF DESCRIPTION OF THE DRAWINGS

FIG. 9 is a flowchart showing processing performed in the embodiment.

DETAILED DESCRIPTION

Figure 1:
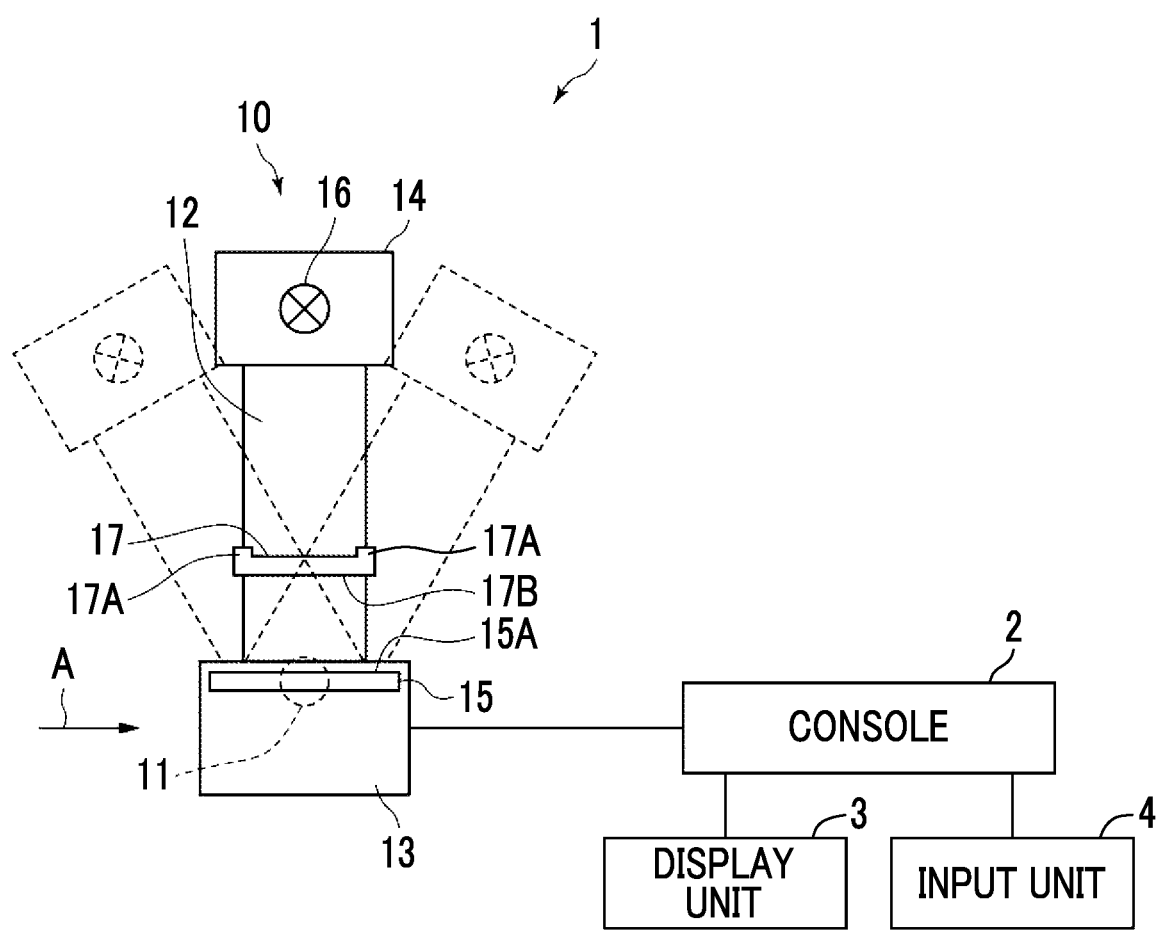
FIG. 1 is a schematic configuration diagram of a radiation image capturing system to which an image processing apparatus according to an embodiment of the present disclosure is applied.
Figure 2:
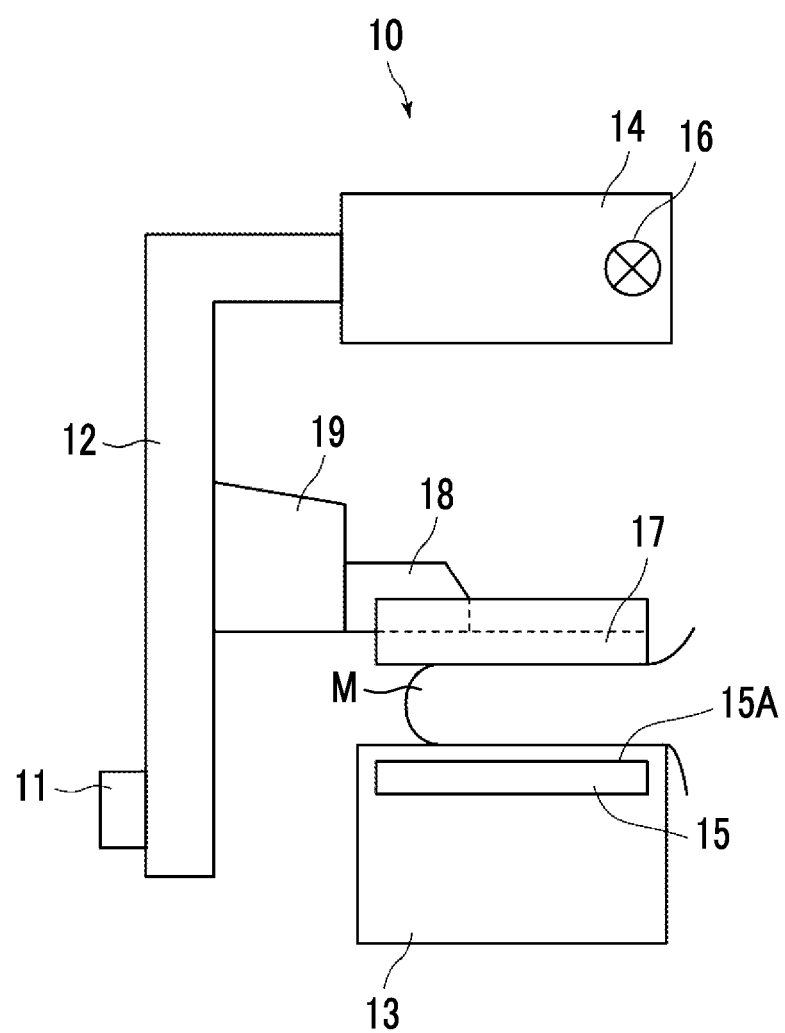
FIG. 2 is a diagram of a mammography apparatus as viewed from the direction of arrow A in FIG. 1.

Hereinafter, the embodiment of the present disclosure will be described with reference to the diagrams. FIG. 1 is a schematic configuration diagram of a radiation image capturing system to which an image processing apparatus according to an embodiment of the present disclosure is applied, and FIG. 2 is a diagram of a mammography apparatus included in the radiation image capturing system as viewed from the direction of arrow A in FIG. 1.

As shown in FIG. 1, a radiation image capturing system 1 according to the present embodiment comprises a console 2 and a mammography apparatus 10. The console 2 comprises a display unit 3 and an input unit 4.

The radiation image capturing system 1 according to the present embodiment has a function of acquiring a breast image that is a radiation image of a breast by the mammography apparatus 10 that images the breast by an operator such as doctors and radiologists based on instructions (imaging orders) input from an external system (for example, a radiology information system (RIS)) via the console 2. In the present embodiment, the mammography apparatus 10 performs both tomosynthesis imaging and simple imaging in various imaging direction, and can generate a tomographic image of the breast and a two-dimensional breast image. The two-dimensional breast image refers to the breast image acquired by simple imaging.

The mammography apparatus 10 comprises an arm unit 12 connected to a base (not shown) by a rotary shaft 11. An imaging table 13 is attached to one end portion of the arm unit 12, and a radiation emission unit 14 is attached to the other end portion so as to face the imaging table 13. The arm unit 12 is configured so that only the end portion to which the radiation emission unit 14 is attached can rotate. Therefore, it is possible to rotate only the radiation emission unit 14 with the imaging table 13 fixed. The rotation of the arm unit 12 is controlled by the console 2.

The imaging table 13 comprises a radiation detector 15 such as a flat panel detector therein. The radiation detector 15 has a detection surface 15A of radiation. In addition, a circuit board on which a charge amplifier for converting a charge signal read from the radiation detector 15 into a voltage signal, a correlated double sampling circuit for sampling the voltage signal output from the charge amplifier, an analog digital (AD) conversion unit for converting the voltage signal into a digital signal, and the like are provided is provided inside the imaging table 13.

The radiation detector 15 can perform recording and reading of a radiation image repeatedly. A so-called direct-type radiation detector that directly converts radiation into electric charges may be used, or a so-called indirect-type radiation detector that converts radiation into visible light and then converts the visible light into a charge signal may be used. As a method of reading a radiation image signal, it is desirable to use a so-called thin film transistor (TFT) reading method in which a radiation image signal is read by ON and OFF of a TFT switch, or a so-called optical reading method in which a radiation image signal is read by emission of reading light. However, other methods may also be used without being limited to the above methods.

A radiation source 16 is housed inside the radiation emission unit 14. The radiation source 16 emits radiation such as X-rays, and the timing of emission of radiation from the radiation source 16, and a radiation generation condition in the radiation source 16, that is, selection of target and filter materials, a tube voltage, an emission time, and the like are controlled by the console 2.

The arm unit 12 includes compression plate 17 that compresses a breast M, a support unit 18 that supports the compression plate 17, and a moving mechanism 19 that moves the support unit 18 in the vertical direction in FIGS. 1 and 2. Information of the distance between the compression plate 17 and the imaging table 13, that is, a compression thickness is input to the console 2. The compression plate 17 is prepared in a plurality of sizes and shapes according to the type of imaging. The compression plate 17 is exchangeably attached to the support unit 18. Side walls 17A are formed at edges of the compression plate 17 which are positioned in right and left portions in FIG. 1. The side walls 17A are formed to reduce the pain of the patient in a case where the breast M compressed by a compression surface 17B of the compression plate 17 protrudes from the compression plate 17.

The display unit 3 is a display such as a cathode ray tube (CRT) or a liquid crystal display, and displays a message required for the operation, and the like in addition to the tomographic image and the composite two-dimensional image described later. The display unit 3 may include a speaker for outputting sound.

The input unit 4 includes an input device such as a keyboard, a mouse, or a touch panel, and receives an operation instruction of the mammography apparatus 10 by the operator. In addition, the input unit 4 receives an input of various kinds of information such as imaging conditions and correcting instruction for information, which are required to perform the tomosynthesis imaging. In the present embodiment, each unit of the mammography apparatus 10 operates according to the information input by the operator through the input unit 4.

An image processing program according to the present embodiment is installed in the console 2. In the present embodiment, the console 2 may be a workstation or a personal computer that is directly operated by the operator, or may be a server computer connected to these through a network. The image processing program is stored in a storage device of a server computer connected to the network, or in a network storage so as to be accessible from the outside, and is downloaded and installed in the computer as necessary. Alternatively, the image processing program is distributed in a state of being recorded on a recording medium such as a digital versatile disc (DVD) or a compact disc read only memory (CD-ROM), and is installed in the computer from the recording medium.

Figure 3:
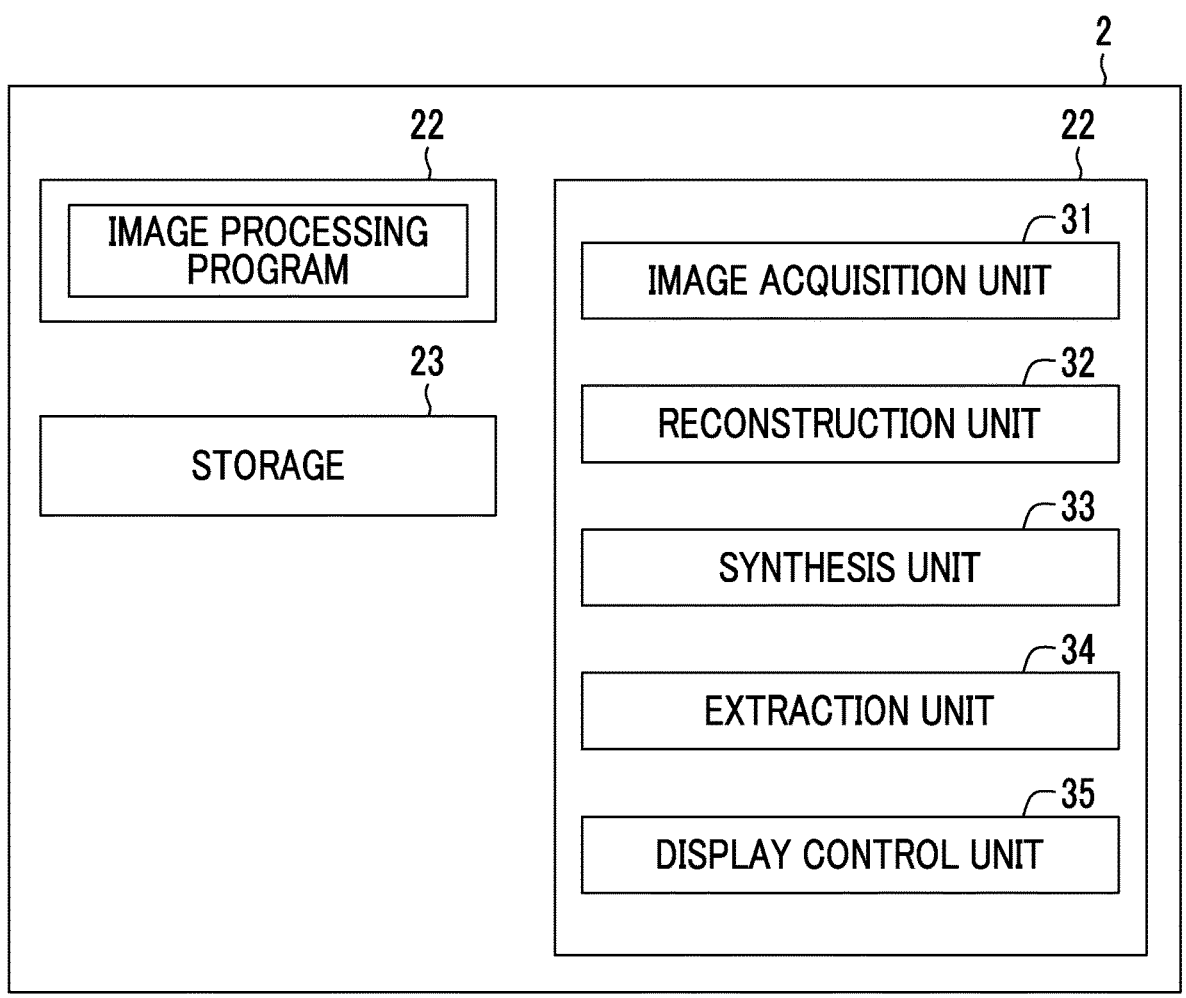
FIG. 3 is a diagram showing a schematic configuration of the image processing apparatus realized by installing an image processing program in a computer that configures a console in the embodiment.

FIG. 3 is a diagram showing a schematic configuration of the image processing apparatus realized by installing the image processing program according to the present embodiment in a computer that configures the console 2. As shown in FIG. 3, the image processing apparatus comprises a central processing unit (CPU) 21, a memory 22, and a storage 23 as the configuration of a standard computer.

The storage 23 includes a storage device such as a hard disk drive or a solid state drive (SSD), and stores various kinds of information including a program for driving each unit of the mammography apparatus 10 and the image processing program. In addition, the storage 23 also stores the projection image acquired by imaging, and the tomographic image and the composite two-dimensional image generated as described later.

The memory 22 temporarily stores programs and the like stored in the storage 23 so that the CPU 21 executes various kinds of processing. The image processing program causes the CPU 21 to execute follows: image acquisition processing of acquiring a plurality of projection images of the breast M corresponding to a plurality of radiation source positions by tomosynthesis imaging by the mammography apparatus 10; reconstruction processing of reconstructing the plurality of projection images to generate a plurality of tomographic images on each of a plurality of tomographic planes of the breast M as a subject; synthesis processing of generating the composite two-dimensional image from the plurality of tomographic images; extracting processing of extracting the mammary gland and calcification from a plurality of tomographic images; and display processing of displaying the composite two-dimensional image on the display unit 3.

Then, the CPU 21 executes these kinds of processing according to the image processing program, so that the CPU 21 of the console 2 functions as an image acquisition unit 31, a reconstruction unit 32, a synthesis unit 33, an extraction unit 34, and a display control unit 35.

Figure 4:
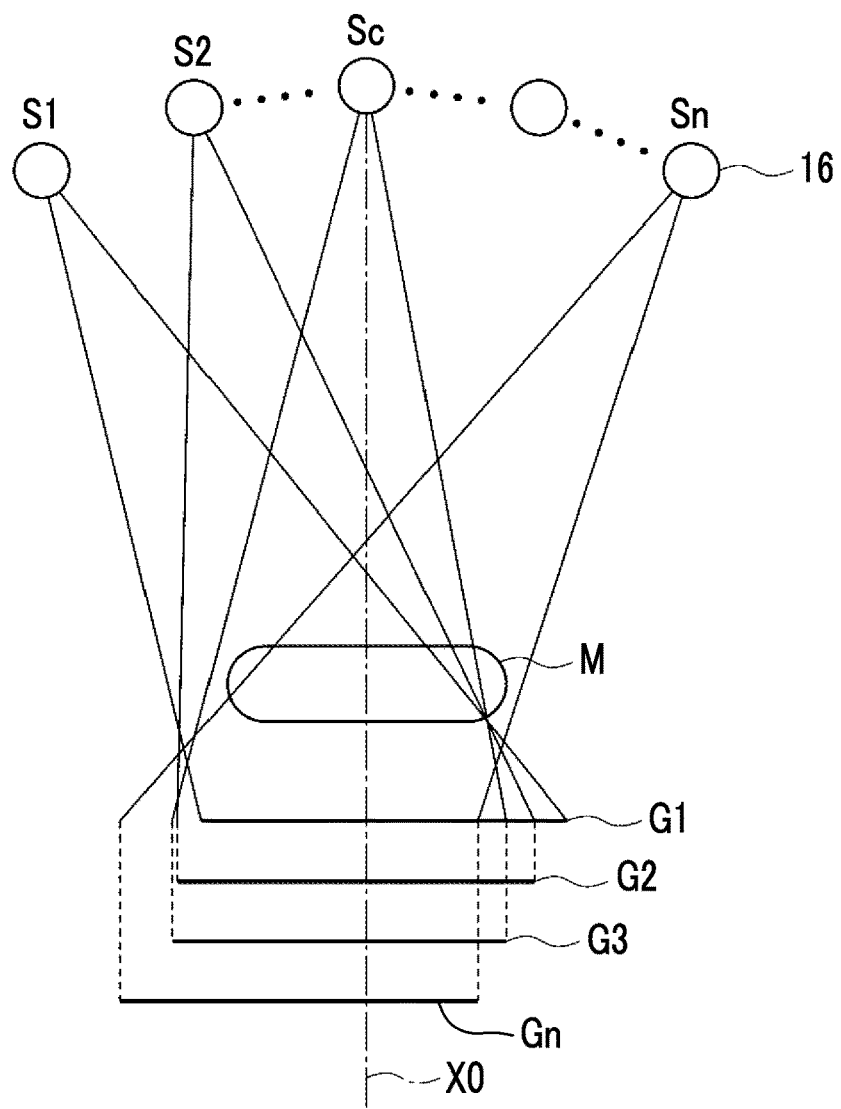
FIG. 4 is a diagram illustrating acquisition of a projection image.

The radiation source 16 is moved by rotating the arm unit 12 around the rotary shaft 11, the breast M as a subject is irradiated with radiation at a plurality of radiation source positions according to the movement of the radiation source 16 under the predetermined imaging conditions for tomosynthesis imaging, radiation transmitted through the breast M are detected by the radiation detector 15, and a plurality of projection images Gi (i=1 to n, where n is the number of radiation source positions; for example, n=15) at a plurality of radiation source positions are acquired by the image acquisition unit 31. FIG. 4 is a diagram illustrating acquisition of the projection image Gi. As shown in FIG. 4, the radiation source 16 is moved to each radiation source position of S1, S2, . . . Sc, . . . , Sn, the radiation source 16 is driven at each radiation source position to irradiate the breast M with radiation, and the radiation transmitted through the breast M are detected by the radiation detector 15. As a result, the projection images G1, G2, . . . Gc, . . . , Gn are acquired corresponding to the radiation source positions S1 to Sn. The radiation source position Sc shown in FIG. 4 is a radiation source position where an optical axis X0 of the radiation emitted from the radiation source 16 is perpendicular to the detection surface 15A of the radiation detector 15. Hereinafter, the radiation source position Sc will be referred to as a reference radiation source position Sc. At each of the radiation source positions S1 to Sn, the breast M is irradiated with radiation of the same dose. A plurality of acquired projection images Gi are stored in the storage 23.

Figure 5:
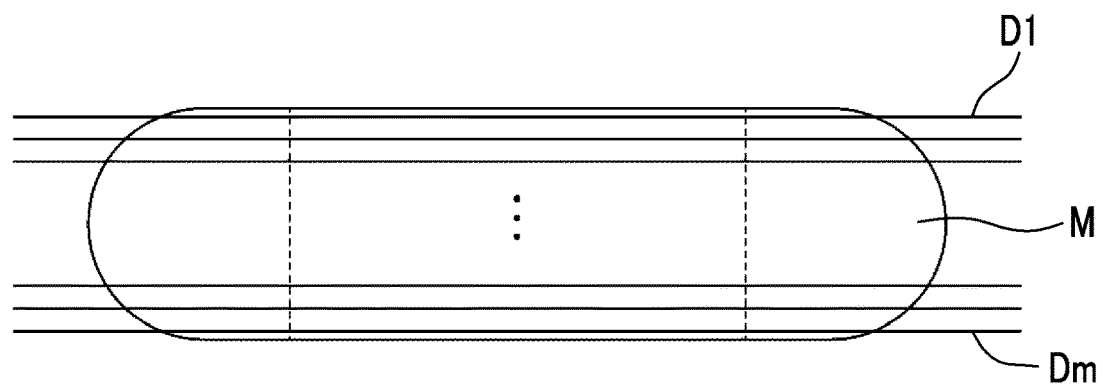
FIG. 5 is a diagram illustrating generation of a tomographic image.

The reconstruction unit 32 reconstructs the projection image Gi to generate the tomographic image in which a desired tomographic plane of the breast M is emphasized. Specifically, the reconstruction unit 32 reconstructs the projection images Gi by a well-known back projection method such as a simple back projection method or a filtered back projection method to generate a plurality of tomographic images Dj (j=1 to m) on each of a plurality of tomographic planes of the breast M, as shown in FIG. 5. In this case, a three-dimensional coordinate position in a three-dimensional space including the breast M is set, pixel values of corresponding pixel positions of a plurality of projection images Gi are reconstructed for the set three-dimensional coordinate position, and the pixel value of the coordinate position is calculated. A three-dimensional image of the breast M is configured by a plurality of tomographic images Dj generated by the reconstruction.

The synthesis unit 33 generates the composite two-dimensional image CG0 using a plurality of tomographic images Dj. The composite two-dimensional image CG0 is a pseudo two-dimensional image corresponding to a simple two-dimensional image captured by irradiating the breast M with radiation from the reference radiation source position Sc. In the present embodiment, the synthesis unit 33 generates the composite two-dimensional image CG0 by the addition method. The addition method is a method of weighted-adding pixel values of pixels corresponding each tomographic image Dj along the viewpoint direction from the reference radiation source position Sc to the radiation detector 15, that is, along an optical axis X0 shown in FIG. 4, in a state where a plurality of tomographic images Dj are stacked. In the addition method, the weight for each pixel at the time of weighted-adding is set to 1/m in a case where m is the number of tomographic images Dj. The method of generating the composite two-dimensional image CG0 is not limited to the addition method, and a known technique can be applied.

The extraction unit 34 extracts the mammary gland and calcification from a plurality of tomographic images Dj. In the present embodiment, the mammary gland and calcification are extracted by using algorithm of known computer aided diagnosis (CAD). For example, the mammary gland is a tubular tissue, and the signal value in the tomographic image Dj is lower than the signal value of fat (that is, the luminance is higher). Therefore, the extraction unit 34 extracts, as the mammary gland, a tubular tissue having a continuously low signal value from a three-dimensional image composed of a plurality of tomographic images Dj. In the present embodiment, the lobule at the end of the mammary gland is also extracted as a part of the mammary gland, but the lobule may not be extracted as a part of the mammary gland.

The extraction unit 34 uses the shape filter corresponding to the calcification shadow to extract the calcification area from the three-dimensional image composed of a plurality of tomographic images Dj, for example, by the method disclosed in JP2002-099896A.

The extraction unit 34 may comprise a discriminator that has been trained to extract the mammary gland and calcification by deep learning, and may extract the mammary gland and calcification from the three-dimensional image composed of a plurality of tomographic images Dj by using the discriminator.

Figure 6:
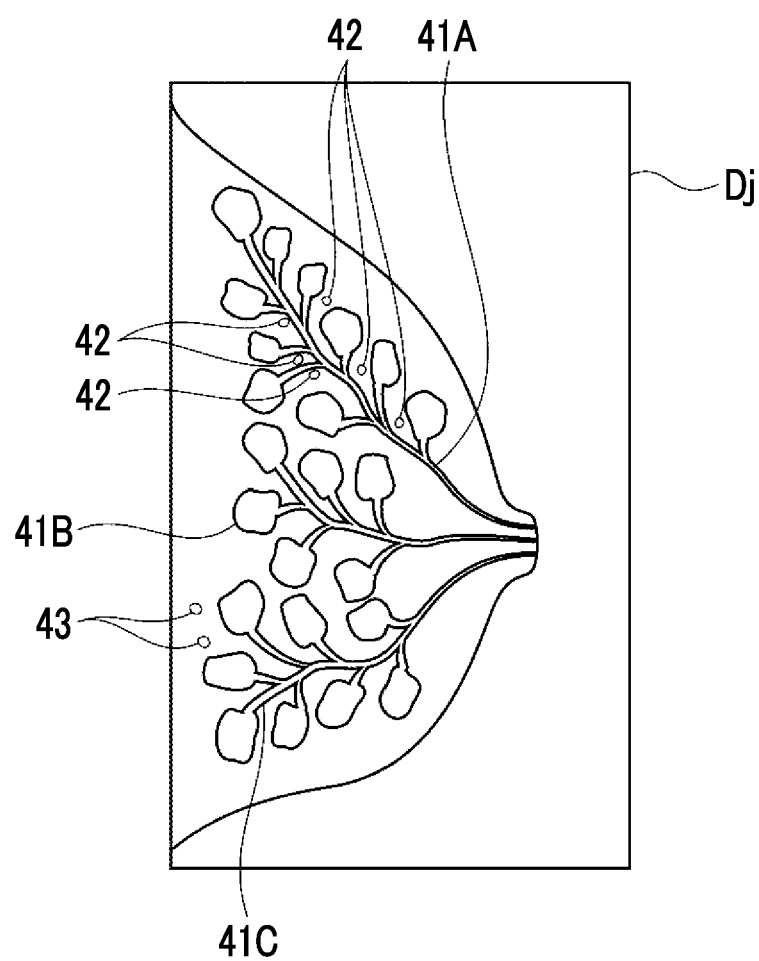
FIG. 6 is a diagram showing a display screen for the composite two-dimensional image.

Calcification is often relatively benign in a case of occurring sporadically in the breast. On the other hand, in a case where calcification is distributed along the mammary gland, calcification is often associated with the mammary gland and is malignant. Therefore, in the present embodiment, the extraction unit 34 associates the extracted mammary gland with the calcification. FIG. 6 is a diagram for explaining the association between mammary glands and calcification. In FIG. 6, for the sake of explanation, in the tomographic image Dj, three mammary glands 41A to 41C are extracted from the breast M, a plurality of calcifications 42 are extracted along the mammary gland 41A, and calcification 43 near the chest wall is extracted. Although the mammary gland and calcification also exist three-dimensionally in the direction in which the tomographic images Dj are arranged (that is, in the thickness direction of the breast M), in FIG. 6, for the sake of explanation, the mammary gland and calcification present in the thickness direction of the breast M are shown to be included in one tomographic image Dj. In FIG. 6, bag-like lobules are extracted at the ends of the mammary glands 41A to 41C.

The extraction unit 34 associates calcification within a predetermined distance from each of the mammary glands 41A to 41C with the mammary gland. In FIG. 6, since the calcifications 42 exist along the mammary gland 41A, the mammary gland 41A and the calcifications 42 are associated with each other. The calcification 43 is at a position away from any of the mammary glands 41A to 41C, and thus, the calcification 43 is not associated with any of the mammary glands 41A to 41C.

Figure 7:
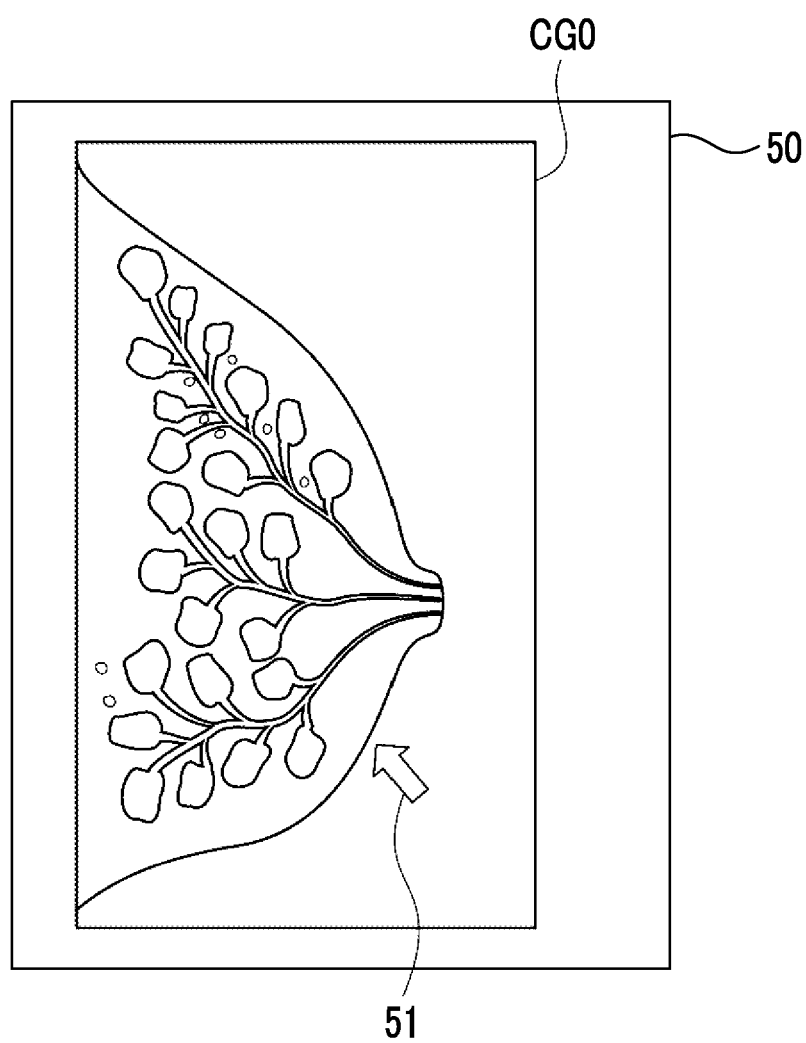
FIG. 7 is a diagram showing a display screen for the composite two-dimensional image.
Figure 8:
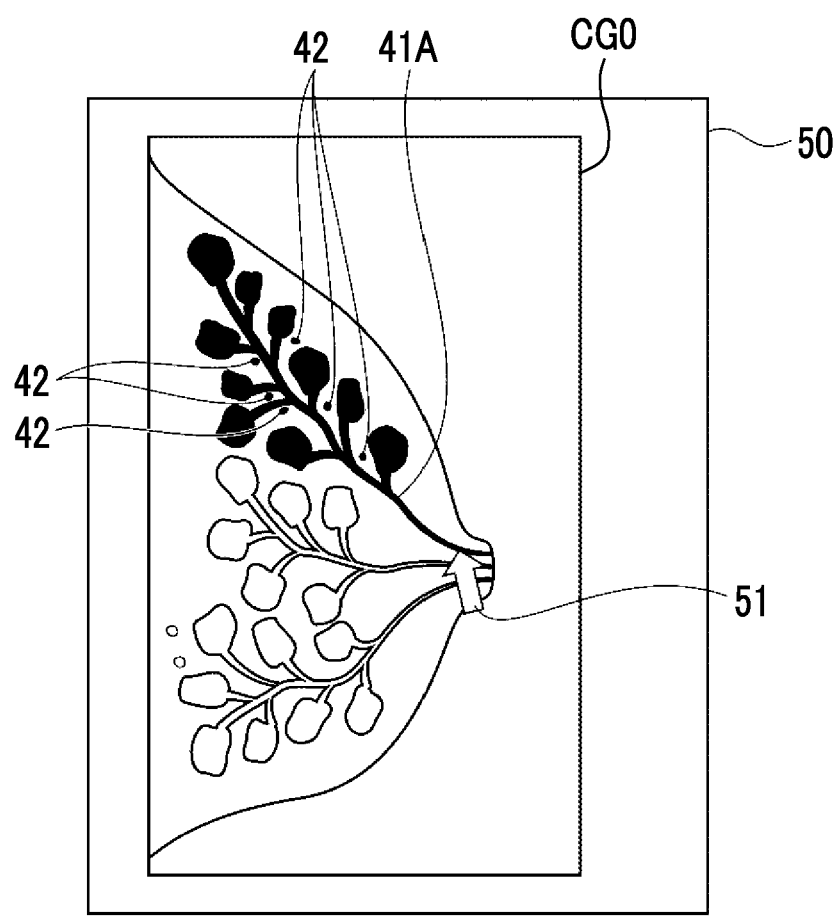
FIG. 8 is a diagram showing a display screen for the composite two-dimensional image.

The display control unit 35 displays the composite two-dimensional image CG0 on the display unit 3. FIG. 7 is a diagram showing the composite two-dimensional image displayed on the display unit 3. As shown in FIG. 7, the composite two-dimensional image CG0 is displayed in a display screen 50. In this state, in a case where a cursor 51 moves to the position of the mammary gland 41A according to an instruction from the input unit 4 and the mammary gland 41A is selected, as shown in FIG. 8, the mammary gland 41A and the calcifications 42 associated with the mammary gland 41A are emphasized and displayed. Emphasized display can be performed, for example, by masking, increasing the luminance, or adding hatching the selected mammary gland 41A and calcifications 42. In FIG. 8, the mammary gland 41A and the calcifications 42 are emphasized and displayed by painting the mammary gland 41A and the calcifications 42 in black.

On the other hand, in a case where the calcifications 42 are selected in the displayed composite two-dimensional image CG0, the display control unit 35 emphasizes and displays the mammary gland 41A associated with the selected calcifications 42. At this time, all the calcifications associated with the mammary gland 41A may be emphasized and displayed, or only the selected calcifications may be emphasized and displayed.

Next, the processing performed in the present embodiment will be described. FIG. 9 is a flowchart showing processing performed in the present embodiment. In a case where the instruction of an operator to start the processing is received through the input unit 4, the tomosynthesis imaging is performed and the image acquisition unit 31 acquires a plurality of projection images Gi (step ST1). The reconstruction unit 32 reconstructs a plurality of projection images Gi to generate a plurality of tomographic images Dj in a plurality of tomographic planes of the breast M (step ST2). The synthesis unit 33 synthesizes a plurality of tomographic images Dj to generate the composite two-dimensional image CG0 (step ST3). The extraction unit 34 extracts the mammary gland and calcifications from a plurality of tomographic images Dj (step ST4). The processing of step ST4 may be performed before step ST3, or may be performed in parallel with step ST3.

The display control unit 35 displays the composite two-dimensional image CG0 on the display unit 3 (step ST5). Subsequently, the display control unit 35 determines whether the mammary gland or the calcification included in the composite two-dimensional image CG0 is selected by the operator (step ST6). In a case where determination in step ST6 is positive, the selected mammary gland or the selected calcification, and the associated calcification or the associated mammary gland are emphasized and displayed (step ST7). That is, in a case where the mammary gland is selected, the selected mammary gland and the calcification associated with the selected mammary gland are emphasized and displayed. On the other hand, in a case where calcification is selected, the selected calcification and the mammary gland associated with the selected calcification are emphasized and displayed.

On the other hand, in a case where determination in step ST6 is negative, the processing proceeds to step ST8. The display control unit 35 determines whether the operator gives an end instruction (step ST8), in a case where determination in step ST8 is negative, the processing returns to step ST6 and the processing from step ST6 is repeated. In a case where determination in step ST8 is positive, the processing ends.

In the present embodiment, the composite two-dimensional image CG0 is displayed on the display unit 3, and in a case where one tissue of the mammary gland or calcification present in association with each other in the breast M in the displayed composite two-dimensional image CG0 is selected, the selected one tissue and the other tissue associated with the selected tissue are emphasized and displayed. Therefore, it is possible to easily recognize the relevance of the mammary gland and the calcification included in the breast M included in the composite two-dimensional image CG0.

In the above embodiment, the extraction unit 34 extracts the mammary gland and the calcification from the tomographic image Dj using CAD, but is not limited thereto. The extraction unit 34 may extract the selected mammary gland and the calcification by displaying the tomographic image Dj on the display unit 3, and selecting the mammary gland and the calcification included in the tomographic image Dj using the input unit 4 by the operator.

In the above embodiment, the addictive method is applied as a method of generating the composite two-dimensional image by the synthesis unit 33, but other known techniques can be applied as described above. For example, a so-called minimum path method using the minimum value of the corresponding pixels of each tomographic image may be applied.

The radiation in the above embodiment is not particularly limited, and α-rays or γ-rays can be applied in addition to X-rays.

In the embodiment described above, for example, various processors shown below can be used as the hardware structures of processing units that execute various kinds of processing, such as the image acquisition unit 31, the reconstruction unit 32, the synthesis unit 33, the extraction unit 34, and the display control unit 35. The various processors include not only the above-described CPU, which is a general-purpose processor that executes software (program) and functions as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of the various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units by one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by one or more of the above-described various processors as a hardware structure.

More specifically, as the hardware structure of these various processors, it is possible to use an electrical circuit (circuitry) in which circuit elements such as semiconductor elements are combined.

What is claimed is:

1. An image processing apparatus comprising at least one processor, wherein the processor is configured to:
   generate a plurality of tomographic images representing a plurality of tomographic planes of a subject by reconstructing a plurality of projection images corresponding to a plurality of radiation source positions which are generated by causing an imaging apparatus to perform tomosynthesis imaging in which a radiation source is moved relative to a detection unit to irradiate the subject with radiation at the plurality of radiation source positions according to movement of the radiation source;
   synthesize the plurality of tomographic images to generate a composite two-dimensional image; and
   display the composite two-dimensional image on a display, and in a case where one tissue of a first tissue and a second tissue that are present in the subject in association with each other is selected in the displayed composite two-dimensional image, emphasize and displays the selected one tissue and the other tissue associated with the selected one tissue.

2. The image processing apparatus according to claim 1, wherein the processor is configured to generate the composite two-dimensional image by weighted-adding pixel values of pixels corresponding to the plurality of tomographic images.

3. The image processing apparatus according to claim 1, wherein the processor is further configured to extract the first tissue and the second tissue from the plurality of tomographic images.

4. The image processing apparatus according to claim 3, wherein the processor is configured to extract the first tissue and the second tissue based on an instruction by an operator with respect to the plurality of tomographic images displayed on the display.

5. The image processing apparatus according to claim 1, wherein the subject is a breast,
   the first tissue is a mammary gland, and
   the second tissue is calcification.

6. An image processing method comprising:
   generating a plurality of tomographic images representing a plurality of tomographic planes of a subject by reconstructing a plurality of projection images corresponding to a plurality of radiation source positions which are generated by causing an imaging apparatus to perform tomosynthesis imaging in which a radiation source is moved relative to a detection unit to irradiate the subject with radiation at the plurality of radiation source positions according to movement of the radiation source;
   synthesizing the plurality of tomographic images to generate a composite two-dimensional image; and
   displaying the composite two-dimensional image on a display, and in a case where one tissue of a first tissue and a second tissue that are present in the subject in association with each other is selected in the displayed composite two-dimensional image, emphasizing and displaying the selected one tissue and the other tissue associated with the selected one tissue.

7. A non-transitory computer-readable storage medium that stores an image processing program causing a computer to execute:
 a procedure of generating a plurality of tomographic images representing a plurality of tomographic planes of a subject by reconstructing a plurality of projection images corresponding to a plurality of radiation source positions which are generated by causing an imaging apparatus to perform tomosynthesis imaging in which a radiation source is moved relative to a detection unit to irradiate the subject with radiation at the plurality of radiation source positions according to movement of the radiation source;
 a procedure of synthesizing the plurality of tomographic images to generate a composite two-dimensional image; and
 a procedure of displaying the composite two-dimensional image on a display, and in a case where one tissue of a first tissue and a second tissue that are present in the subject in association with each other is selected in the displayed composite two-dimensional image, emphasizing and displaying the selected one tissue and the other tissue associated with the selected one tissue.

* * * * *